United States Patent [19]

Ben-Zeev et al.

[11] 4,149,079
[45] Apr. 10, 1979

[54] METHOD OF AND MEANS FOR SCANNING A BODY TO ENABLE A CROSS-SECTION THEREOF TO BE RECONSTRUCTED

[75] Inventors: Dan Ben-Zeev; Zvi Beer; Dan Inbar, all of Haifa, Israel

[73] Assignee: Elscint, Ltd., Haifa, Israel

[21] Appl. No.: 705,250

[22] Filed: Jul. 14, 1976

[51] Int. Cl.² .................. A61B 6/02; G01N 23/08
[52] U.S. Cl. ........................ 250/445 T; 250/252; 250/360
[58] Field of Search .............. 250/362, 403, 445 T, 250/363, 369, 360, 252

[56] References Cited

U.S. PATENT DOCUMENTS

| | | | |
|---|---|---|---|
| 3,924,129 | 12/1975 | Lemay | 250/445 T |
| 3,952,201 | 4/1976 | Hounsfield | 250/403 |
| 3,956,633 | 5/1976 | Hounsfield | 250/362 |
| 3,973,128 | 8/1976 | Lemay | 250/445 T |
| 4,008,400 | 2/1977 | Brunnett et al. | 250/445 T |
| 4,035,651 | 6/1977 | Lemay | 250/445 T |

*Primary Examiner*—Alfred E. Smith
*Assistant Examiner*—T. N. Grigsby
*Attorney, Agent, or Firm*—Donald M. Sandler

[57] ABSTRACT

A fan beam of the type described herein is oriented so as to be coplanar with the cross-section of a body to be reconstructed. Pure rotational movement is imparted to the fan beam by rotating the same about a fixed center of rotation such that the fan beam sweeps out an area in the plane of the cross-section; and the absorption coefficients over such area can be computed in a known manner from measurements of the intensities of the beams emerging from the area swept out thereby.

When one extremity of the fan beam passes through the fixed center of rotation, the area swept-out by the fan beam during one revolution thereof is circular, the center of which is coincident with the fixed center and the periphery of which is tangent to the other extremity of the fan beam. When the fixed center lies outside the fan beam, the area swept-out is annular and is defined by concentric circles whose centers are coincident with the fixed center and whose peripheries are respectively tangent to the extremities of the fan beam.

By sequentially rotating the fan beam about the fixed center, and shifting the fan beam relative thereto after each revolution (e.g., by rotating the fan beam about its apex), a circular area of arbitrary size can be swept-out by the fan beam after a number of revolutions. The size of such area is thus independent of the apical angle of the fan beam.

34 Claims, 8 Drawing Figures

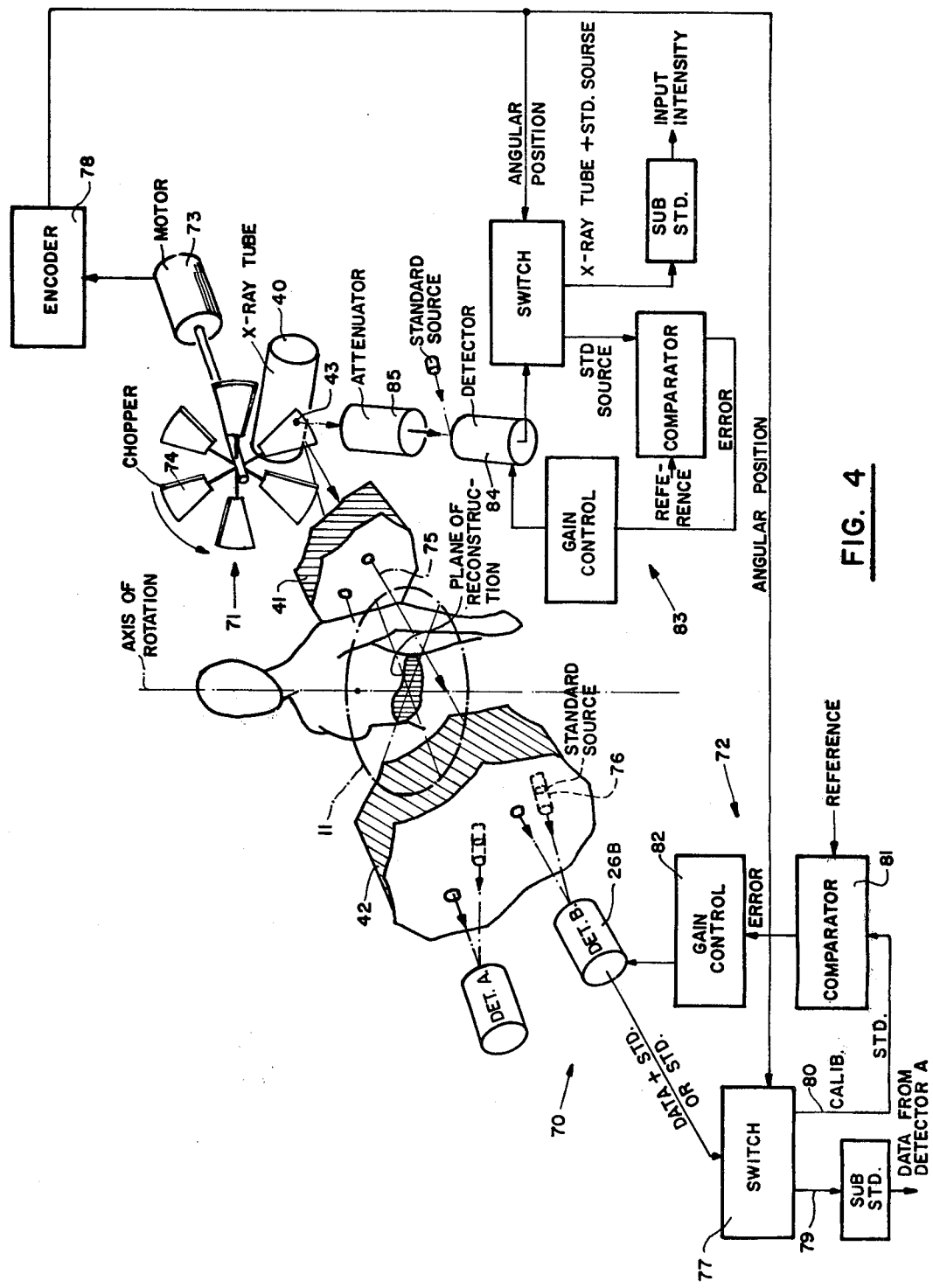

METHOD OF AND MEANS FOR SCANNING A BODY TO ENABLE A CROSS-SECTION THEREOF TO BE RECONSTRUCTED

CROSS-REFERENCE MATERIAL

The following publications are hereby incorporated by reference:

[1] Ein-Gal, Moshe; "The Shadow Transform: An Approach to Cross-Sectional Imaging", Technical Report SEL-74-050, Information Systems Laboratory, November 1974.

[2] Brooks, R. A. and DiChiro, G., "Theory of Image Reconstruction in Computed Tomography", *Radiology*, Vol. 117, pages 561–572, Dec. 1975.

BACKGROUND OF THE INVENTION

This invention relates to a method of and means for scanning a body with penetrating radiation to enable a cross-section thereof to be reconstructed in terms of the distribution over the cross-section of the coefficients of absorption with respect to such radiation.

U.S. Pat. No. 3,934,142 shows a scanner for obtaining such a distribution utilizing a scanner head assembly comprising a point source of penetrating radiation and a planar array of detectors spatially fixed with respect to the source and located at discrete angular positions with respect to the source. Those beams from the source incident on the detectors establish a plurality of discrete, coplanar pencil beams of penetrating radiation defining a planar fan beam.

The head assembly is positioned so that the medial beam of the fan beam passes through a fixed center about which the head assembly is rotatable in the plane of the detectors. During a complete revolution of the head assembly, the source moves in a circle concentric with the fixed center and the fan beam sweeps out an area, in the plane of the detectors, over which the absorption coefficients with respect to the penetrating radiation can be computed by any of several known reconstruction algorithms, such as those described in reference [2], operating on the outputs of the detectors. The area swept out by the fan beam is contained within a circle, termed the circle of reconstruction, such circle being coplanar with the fan-beam and having its center coincident with the fixed center and its periphery tangent to the beams defining the extremities of the fan beam. In a given scanner, the diameter of the circle of reconstruction is directly related to the apical angle of the fan beam, i.e., the angle between the extremities of the fan beam.

When a living body is placed in the circle of reconstruction, a cross-section through the body in the plane of the circle of reconstruction can be reconstructed using the scanning technique described above. In order to minimize the radiation dosage applied to the living body, all beams from the source except those incident on the detectors are blocked by a pre-collimator interposed between the source and the body. When a section through a non-living body, such as an industrial object, is to be reconstructed, the pre-collimator is optional. Regardless of the nature of the body being examined, only those beams incident on the detectors contribute to the outputs of the detectors. For this reason, the term "fan-beam of the type described", as used hereinafter, means either a group of discrete coplanar pencil beams of penetrating radiation produced by a collimator to which a fan of radiation from a point source is applied, or those discrete coplanar beams of a fan of radiation produced by a point source and incident on a planar array of detectors when no collimator is used. Furthermore, the term "penetrating radiation" as used hereinafter, is a term of convenience intended to cover radiation that penetrates such as, but not limited to, X-rays from an X-ray tube as well as gamma rays from a nuclear source. Finally, unless otherwise specified, the term "intensity of a beam of a fan beam" means the intensity of the beam incident on a detector and is thus used to designate the intensity of a beam emerging from the area swept out by the fan beam during its rotation relative to a fixed center, as distinguished from the intensity of the beam produced by the source. A beam emerging from such area may be attenuated or not depending upon whether the beam has passed through a body located in the area.

A scanner having a head assembly that produces a fan beam of the type described is, hereinafter, termed a scanner of the type described. When a scanner of the type described is arranged so that the head assembly is rotatable about a spatially fixed center, the scanner is said to have a scan utilizing pure rotational movement. Such a scan carried out by a scanner of the type described, wherein the medial beam of the fan beam passes throught the fixed center is, hereinafter, termed a scan of the type described.

The physical size of a scanner of the type described, which carries out a scan of the type described, is dependent on the size of the circle of reconstruction which, as pointed out above, is dependent on the apical angle of the fan beam. The size of the circle of reconstruction is dictated by the largest body to be scanned; and the apical angle of the fan beam is dictated by the nature of the source to be used. In medical equipment for scanning a human torso, the circle of reconstruction must be about 500 mm in diameter, while for scanning a human head, a circle of reconstruction of about 250 mm is adequate. The apical angle of conventional X-ray tubes, presently used as the source in conventional scanners of the type described, is about 40° requiring the source to be rotatable along a circular path about two meters in diameter for a torso scanner. When the supporting structure for the head assembly is taken into account, the scanner stands about three meters high by about three meters wide, a rather formidable piece of equipment to say the least. Furthermore, some scanners use as many as 300 detectors, which, with their associated electronic circuitry, establish a significant mass that must be supported and rotated.

Compared to a torso scanner, a human head scanner with a 40° fan beam, would be about half the physical size. While a finer fan beam is usually employed in a head scanner to improve picture quality and provide more details in the reconstructed cross-section as compared to a torso scanner, only about two-thirds as many detectors are required as compared to a torso scanner. Thus, a head scanner is smaller, lighter and less expensive than a torso scanner.

Torso scanners and head scanners of the type described have been built and are in use for their specialized purposes. A head scan could be carried out in a torso scanner, since its circle of reconstruction is large enough to accommodate a human head; but this is usually not done because the picture quality obtained would be too poor. On the other hand, if a torso scan were required with picture quality comparable to that obtained from a head scanner, it is apparent that the availability of a head scanner would be irrelevant because its circle of reconstruction could not accommodate a torso.

A large medical facility with a need for the ultimate in diagnostic equipment will thus require two separate scanners of the type described, each limited to different portions of a human body. Each scanner is obviously physically large, tremendously expensive, and unfortunately inflexible in use, which is a factor that adds to the financial burden on a medical facility. And notwithstanding all the expense, the picture quality obtained with a torso scanner is not comparable to that obtained with a head scanner.

It is an object of the present invention to provide a new and improved scanner of the type described, and a new and improved scanning technique utilizing pure rotational movement of the head assembly wherein the above-described deficiencies of known scanners of the type described are overcome or substantially reduced.

SUMMARY OF THE INVENTION

According to the present invention, there is provided a method for scanning a body to enable a cross-section thereof to be reconstructed. Such method includes producing, from a point source of penetrating radiation, a fan beam of the type described which has an apical angle $\alpha$, and which is coplanar with, and passes through, the cross-section. Rotation of the fan beam about a fixed center causes the fan beam to sweep out an area in the plane of the cross-section contained within a circle that is tangent to the extremity of the fan beam most remote from the fixed center. The tangents to such circle passing through the source intersect at an apical angle $\beta$. Measuring the intensity of each beam emerging from the area swept out by the fan beam during its rotation enables computation of a representation of the distribution of the absorption coefficients over such area. The improvement in this method comprises the step of selecting the apical angle $\alpha$ such that it is less than the apical angle $\beta$.

When one extremity of the fan beam passes through the fixed center, the area swept out by the fan beam is a circle whose center coincides with the fixed center and whose periphery is tangent to the other extremity of the fan beam. In such case, the apical angle $\alpha$ of the fan beam is one-half the apical angle $\beta$. A fan beam of the type described with an apical angle half that found in a scanner of the type described, when used in accordance with the present invention, will sweep out the same area in one revolution. Moreover, this result is achieved with 50% fewer detectors and associated circuitry. The quality of the reconstructed area can be improved by shifting the fan beam relative to the fixed center, (e.g., by rotating the fan beam about the source until the beams in the new angular position are interleaved with the position of the beams in their former position) and repeating the rotation.

When the fixed center lies outside the fan beam, the area swept-out is annular and is defined by concentric circles whose centers coincide with the fixed center and whose peripheries are respectively tangent to the extremities of the fan beam. By sequentially rotating the fan beam about the fixed center and shifting the fan beam relative thereto after each revolution (e.g., by rotating the fan beam about its apex), a circular area of arbitrary size can be swept out by the fan beam after a number of revolutions. Such area is made up of a composite of sub-areas swept out during each revolution of the fan beam; and its size is independent of the apical angle of the fan beam.

When used in accordance with the present invention, a fan beam of the type described can be used to scan a head, for example, in one revolution, and a torso in two revolutions. Thus, one piece of equipment, comparable in size to a head scanner of the type described, can be used for either head or torso scans resulting in a more efficient relationship between equipment size and expense relative to capability.

The invention also consists in apparatus for carrying out the method described above. Such apparatus includes a movable scanner means having a source of penetrating radiation for producing a fan beam of the type described which has an apical angle $\alpha$, and which is coplanar with, and passes through, the cross-section of the body. Means are provided for rotating the scanner means about a fixed center for causing the fan beam to sweep out an area in the plane of the cross-section contained within a circle tangent to the extremity of the fan beam most remote from the center. The tangents to such circle passing through the source intersect at an apical angle $\beta$. The relationship between the apical angle $\alpha$ and the apical angle $\beta$ is that the apical angle $\alpha$ is less than the apical angle $\beta$.

The invention also consists in apparatus for calibrating the detectors of a scanner of the type described, the improvement comprising means for periodically interrupting the beams of the fan beam, and means for calibrating the detectors during the interval in which the beams are interrupted.

BRIEF DESCRIPTION OF THE DRAWINGS

An embodiment of the present invention is disclosed in the accompanying drawings wherein:

FIG. 4 is a perspective schematic view of apparatus according to the present invention for calibrating a scanner of the type described.

DETAILED DESCRIPTION

Figure 1:
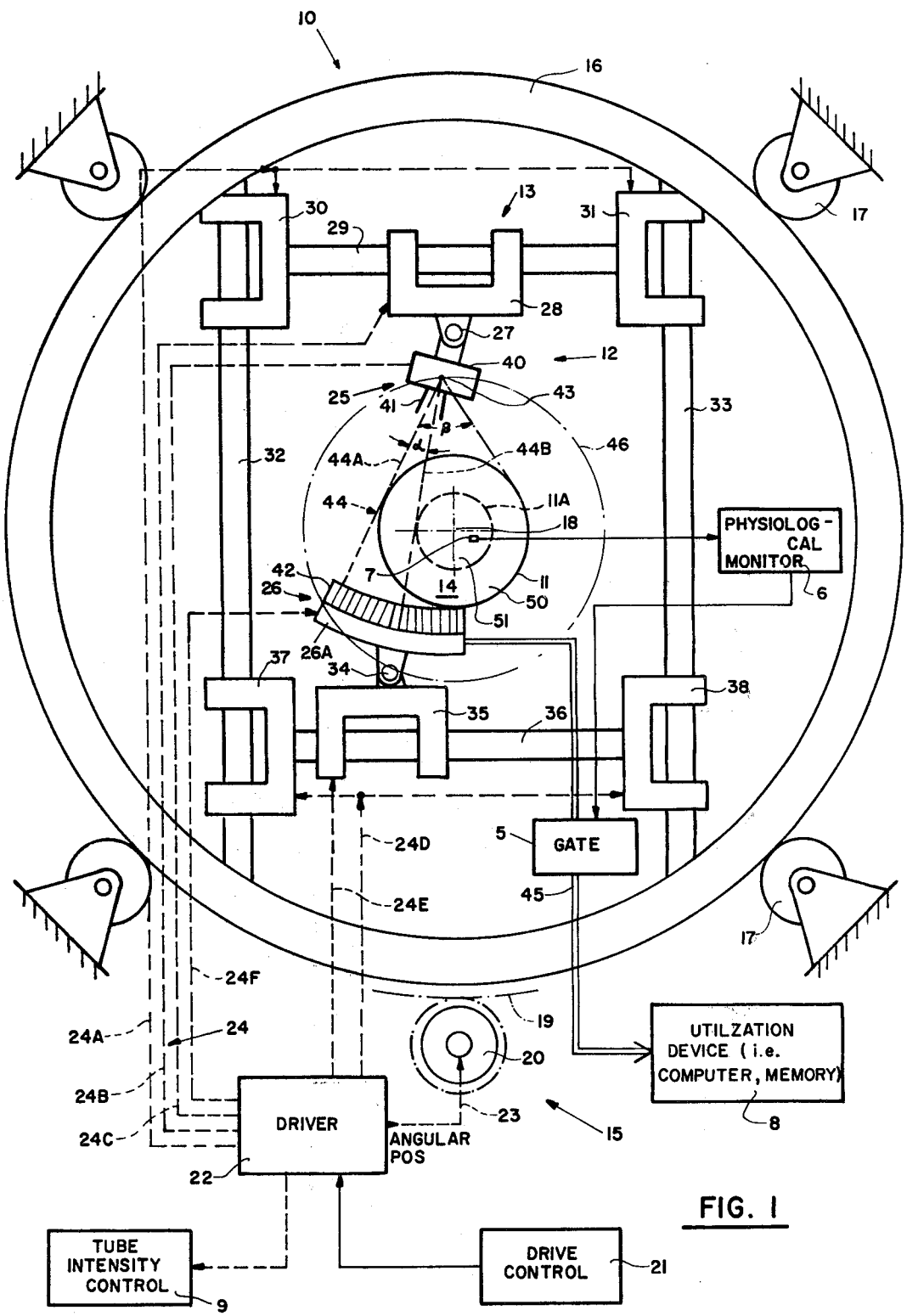
FIG. 1 is a schematic elevation of apparatus according to the present invention for performing a pure rotational movement scan utilizing a fan beam with an apical angle less than the apical angle of the overall circle of reconstruction.

Referring now to FIG. 1, reference numeral 10 designates scanner apparatus according to the present invention for carrying out a pure rotational movement (P.R.M.) scan of a cross-section of an object (not shown), such as a portion of a human torso, or an inanimate object, contained within a cylindrical, non-rotatable housing 11 whose perimeter defines the overall circle of reconstruction of the apparatus. Apparatus 10 includes scanner head assembly 12, mounting means 13 for enabling the scanner head assembly to scan cross-section 14 (i.e., the area within the circle defined by housing 11), and driver means 15 for controlling the scanning and other movements of assembly 12.

Mounting means 13 includes a circular ring member 16 carried by a plurality of bearings 17 mounted in a fixed manner on a stationary support structure such that member 16 is rotatable about its fixed center 18 which coincides with the center of circular housing 11. Driver means 15 includes the toothed outer periphery 19 of member 16 which meshes with the toothed periphery of drive gear 20 rotatably mounted in fixed relationship to center 18. The driver means also includes drive-control 21, whose operation is effected by a computer as described below, and a driver 22 responsive to the drive-control for producing a mechanical output 23 that rotates gear 20, and for producing control signals applied via control lines 24 to the various components of scanner head assembly 12 in the manner described below. By reason of the mechanical output 23, member 16 can be selectively rotated through 360° at a predetermined angular velocity. In addition, axial displacement of member 16 along the axis of rotation passing through center 18 is limited in a conventional manner by thrust bearings of the like (not shown).

Scanner head assembly 12 includes scanner head 25, detector head 26, and mounting means by which the heads are spatially fixed relative to each other, but are selectively capable of being repositioned relative to the fixed center 18 in accordance with the control signals furnished by control lines 24. Scanner head 25 is pivotally mounted at 27 on scanner head carrier 28 which is slidably mounted on rod 29 on whose opposite ends are rigidly mounted upper carriers 30 and 31. Each of these last mentioned carriers are slidably mounted on rods 32, 33 which are rigidly fixed to member 16 such that the mounting rod 29 is perpendicular to the rods 32 and 33.

Detector head 26 is pivotally mounted at 34 to detector head carrier 35 which is slidable on rod 36 on the opposite ends of which are rigidly mounted lower carriers 37 and 38. Carrier 37 is slidable on rod 32, and carrier 38 is slidable on rod 33 such that rods 29 and 36 are maintained in parallel relationship to each other, and in perpendicular relationship to rods 32 and 33.

By reason of the mounting means described above for the heads 25 and 26, each head is orthogonally movable in the plane of cross-section 14, and is also pivotable about an axis parallel to the axis passing through fixed center 18. An interconnection, such as a rack and pinion drive (not shown) between each carrier and the rod on which the carrier is slidable, permits the carrier to be displaced on the rod in response to a control signal in the control line 24 connected to the carrier.

Scanner head 25 may include a conventional X-ray tube 40 producing a solid fan of X-rays having an apical angle of at least α. By means of pre-collimator 41 mounted on X-ray tube 40, and postcollimator 42 mounted on detector head 26, the X-rays entering circle 11 are in the form of a plurality of discrete pencil beams originating at essentially a point indicated at 43 and diverging therefrom into a fan beam 44 with an apical angle α. Only the two beams 44A and 44B defining the extremities of fan beam 44 are shown in FIG. 1 to simplify the drawing. The X-ray tube 40 may produce a time-wise constant output or it may be a pulsed tube to facilitate calibration as explained below. Preferably, the tube intensity (and hence the intensity of the individual beams of the fan beam) is adjustable by tube intensity control 9 in accordance with a control signal from driver 22.

FIG. 1 shows the apical angle of the fan beam to be about 15° and, as indicated below, this angle may be as large as 30°. By changing collimators 41 and 42, and/or the X-ray tube, the apical angle of the fan beam can be changed.

By applying suitable control signals to control lines 24A, 24B, 24C, the point 43 can be positioned at a predetermined distance from the fixed center 18, and the angular position of beam 44 can be adjusted until the beam 44A, most remote from fixed center 18, is tangent to the overall reconstruction circle 11. The fan beam is now in position I shown in FIG. 2A.

Detector head 26 is in the form of a planar array of discrete X-ray detectors (not shown), one for each beam in the fan-beam 44, the individual detectors being aligned with the apertures in postcollimator 42. Control signals applied to control lines 24D, 24E and 24F enable the detector head to be positioned to receive the individual beams from the fan beam 44 on their emergence from the cross-section 14. Thus, detector head 26 has a detector associated with each beam and mounted at discrete angular positions in predetermined relationship to the source contained within the X-ray tube 40.

Figure 2A:
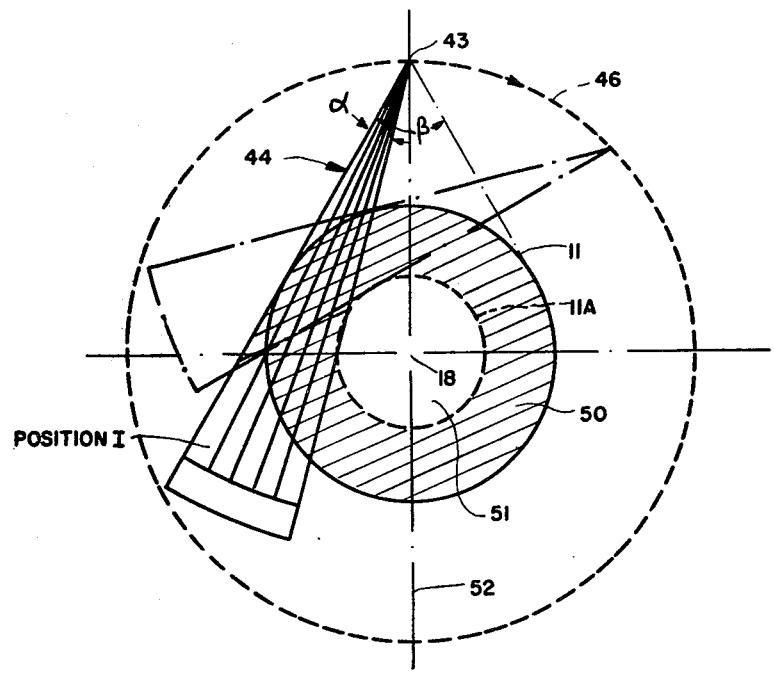
FIG. 2A is a schematic showing of what is termed a quarter-fan beam positioned to sweep out the outer annular portion of the overall circle of reconstruction during one revolution of the fan beam.

When the mechanical input 23 rotates ring member 16 through a complete revolution, point 43 travels in a circular path 46 about the fixed center 18 as the fan beam 44, which is coplanar with the cross-section 14, sweeps out a predetermined area in the plane of the cross-section. Such area is the annular region 50 shown in FIG. 1. This annular region is defined by concentric circles 11 and 11A centered at the fixed center 18 and respectively tangent to the beams 44A and 44B at the extremities of the fan beam. FIG. 2A is an enlarged view of the circle of reconstruction showing the orientation of the fan beam at two locations of the source as it travels along path 46.

During the rotation of ring member 16, each detector accumulates charge while a beam is incident thereon, the charge being periodically measured in a known fashion by an electrometer, for example. The output of the electrometer is preferably digitized in an analog-to-digital-converter. A logarithmic operation may be carried out before or after storage to obtain the intensity of the incident beam. Regardless, data from the detectors is furnished through data lines 45 to a utilization means 8 which may be a memory of a computer programmed to operate on the data and reconstruct area 14.

By utilizing a known algorithm, such as the circular harmonic transform algorithm of reference [1], data obtained after the source has completed one revolution can be operated on to provide a representation of the coefficient of absorption at each elemental area in the annular region 50 through which the fan beam has swept.

Figure 2B:
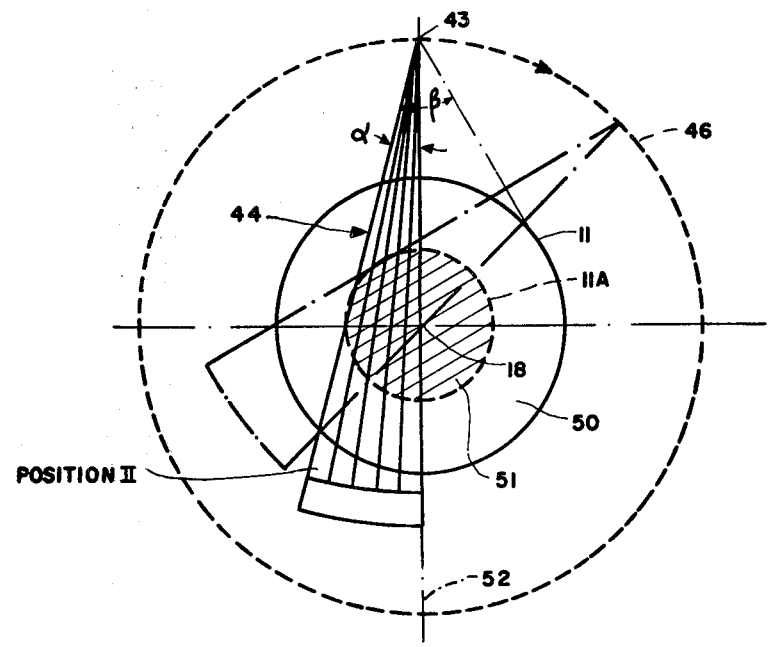
FIG. 2B is similar to FIG. 2A except that the quarter-fan beam has been rotated to a position at which it will sweep out the central portion of the overall circle of reconstruction during one revolution of the fan beam.

Upon completion of the above-described rotational movement, drive control 21 is activated in order to cause driver 22 to shift the source 43 relative to the fixed center such that the fan beam 44 is then positioned to sweep across a different area of the cross-section during the next rotation of ring member 16. Specifically, tube 40 is rotated until beam 44B of the fan beam passes through the fixed center 18, while beam 44A, which is the most remote from the fixed center, is tangent to the circle that had been tangent to beam 44B during the previous rotation of ring 16. Fan beam 44 is now in position II as shown in FIG. 2B, which also shows the fan beam orientation at two locations of the source as it travels along path 46.

For reasons associated with the stability of the detector head 26, it is preferred to utilize the same detectors during the subsequent rotation of ring member 16 as had been used previously. For this reason, carriage 35 is positioned such that the beams of fan beam 44 are detected by the same detectors. Drive control 21 is then activated causing the mechanical output 23 to once more rotate ring member 26 through a complete revolution during which the fan beam will sweep across the circular region 51 defined by the circle of reconstruction 11A. Data obtained during the last mentioned rotation of the source 43 is also measured, converted and stored in the same manner previously described, and utilized in the same way to obtain a representation of the coefficients of absorption within the circle of reconstruction 11A. Upon completion of the second rotation and the computation associated therewith, a representation of the coefficients of absorption across the entire cross-section 14 will have been obtained.

Figure 2C:
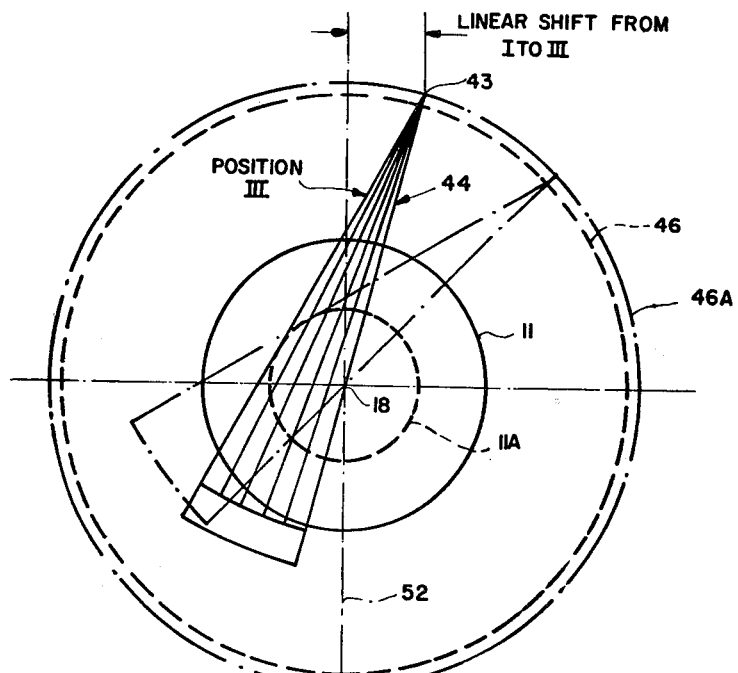
FIG. 2C is similar to FIG. 2A except that the quarter-fan beam has been laterally displaced in order to position it to sweep out the central portion of the circle of reconstruction during one revolution of the fan beam.

Instead of rotating the fan beam through the angle from position I to position II after the annular region 50 has been swept thereby, the fan beam can be shifted relative to center 18 for the purpose of positioning it in such a way as to enable it to sweep across circular region 51. For example, the fan beam can be linearly displaced as shown in FIG. 2C to position III. In such case, the displacement is perpendicular to the line 52 connecting source 43 to center 18. Such a linear shift will position the extremities of the beam as indicated in FIG. 2C with the beam at one extremity passing through the center 18 and the beam at the other extremity being tangent to circle 11A. The linear displacement illustrated in FIG. 2C can be carried out with the mechanism shown in FIG. 1 by suitable control signals applied to carriage 28 and to carriages 30 and 31. In this case, the source 43 travels about the center 18 along the path 46A which is larger in diameter than path 46.

Alternatively, other displacements of the source 43 can be utilized in order to position the fan beam such that one of its extremities passes through the center 18, and the other is tangent to circle 11A. For example, the source 43 can be moved along circular path 46 by suitable adjustment to carriages 28, 30 and 31 to position the source on the circular path 46.

The above-described arrangement of the fan beam is applicable to the situation where the apical angle $\alpha$ of the fan beam is one-quarter of the apical angle $\beta$ of the circle of reconstruction 11. The apical angle of a given circle of reconstruction is the angle between the tangents to the circle passing through the source of the fan beam located at its apex. In general, for a given circle of reconstruction having an apical angle $\beta$, the apical angle $\alpha$ of the fan beam can be selected such that:

$$\alpha = \beta/2n$$

where n = 1, 2, 3, . . . The fan beam is rotated n times about the fixed center (as data are collected during each revolution). After a revolution is completed, the fan beam is rotated through the angle $\alpha$ about the source in the plane of the fan beam. When n−1 rotations have been completed, the fan beam will have swept out a circle of reconstruction having an apical angle $\beta$.

There are two optional modifications that go with the general case just described: one deals with automating the shift of the fan beam at the completion of each revolution depending upon whether the area swept out by the fan beam covers the entire cross-section of the body under investigation; and the other deals with optimizing the dosage in relation to the reconstructed picture quality. The shift of the fan beam is automated by utilizing, for control purposes, the output of detector 26A associated with beam 44A which is at the extremity of the fan beam most remote from the fixed center 18. During a revolution of the scanner head assembly 12, the charge accumulated by detector 26A is measured, converted and stored in the utilization means as a measure of the intensity of beam 44A incident on detector 26A. If such intensity is below a threshold level over at least a portion of a revolution, it is concluded that beam 44A must have passed through attenuating matter during such portion. In such case, the utilization means signals drive control 21 to order driver 22 to rotate the scanner head assembly through the angle $\alpha$ upon completion of one revolution and the fan beam is effective to sweep out another area. The process continues until the monitored intensity over one revolution is above the threshold (indicating an "air" reading), and the utilization means signals drive control 21 that the scan is complete.

The dosage in relation to the reconstructed picture quality is optimized by relating the intensity of radiation entering the area swept out by the fan beam to the path length through such area. To this end, a variable intensity X-ray tube is used in conjunction with intensity control 9. When, for example, the fan beam is sweeping out the center portion of the circle of reconstruction, the path length of the fan beam through such center portion will be shorter than the path length through the next annular portion surrounding the center portion and swept out following rotation of the fan beam through the angle $\alpha$. The particular portion of the circle of reconstruction currently being swept out is determined by the utilization means which sends an appropriate signal to drive control 21 ordering it to cause driver 22 to send an appropriate signal to control 9 which properly adjusts the intensity of tube 40 consistent with the particular portion of the circle of reconstruction being swept out.

The case for n=2 (i.e., $\alpha = \beta/4$) is particularly advantageous in enabling the resultant apparatus to function as either a head or a torso scanner. When the fan beam is in position II shown in FIG. 2B, the area 51 within circle 11A is swept out during one revolution, such circle being large enough to accomodate a human head. As indicated below, provision is made for enhancing the reconstructed cross-section of area 51 by shifting the fan beam to interleave the beams and performing another scan by rotating the fan beam.

When it is desired to scan a torso, the fan beam can be located in position II shown in FIG. 2B and data collected during rotation in this position to cover at least a portion of the cross-section of the torso. Following this scan, the fan beam can be rotated to position I and then rotated about the fixed center to complete the scan. Since it is likely that the central region of the scan will be of greater interest, the reconstruction of such region can be enhanced by the shift described below.

A special situation arises when the apical angle of the fan beam in one-half the apical angle of the circle of reconstruction. This situation is illustrated in FIG. 3A where fan beam 60 is shown oriented with respect to the fixed center 18 such that one extremity 60B of the fan beam passes through fixed center 18 of the circle of reconstruction 11, and the other extremity 60A is tangent to circle 11. With this arrangement, a single rotation of the source 43 along the circular path 46, whose center is at 18, will cause the fan beam to sweep across the area within circle 11, and the output of the detector head will provide sufficient data for computing the coefficients of the absorption over the entire circle of reconstruction 11. The phantom lines in FIG. 3A show the orientation of the fan beam after source 43 has been rotated through 45°.

Figure 3C:
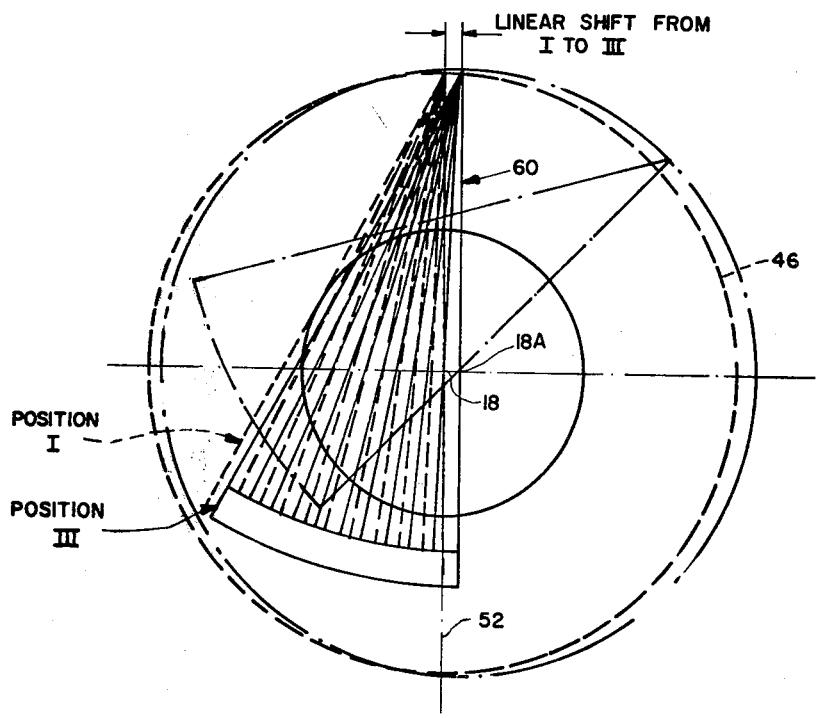
FIG. 3C is similar to FIG. 3A except that the half-fan beam has been laterally shifted by an amount sufficient to displace the beams to a position midway between the original position of the beams in order to increase the density of the data points in the circle of reconstruction.
Figure 3A:
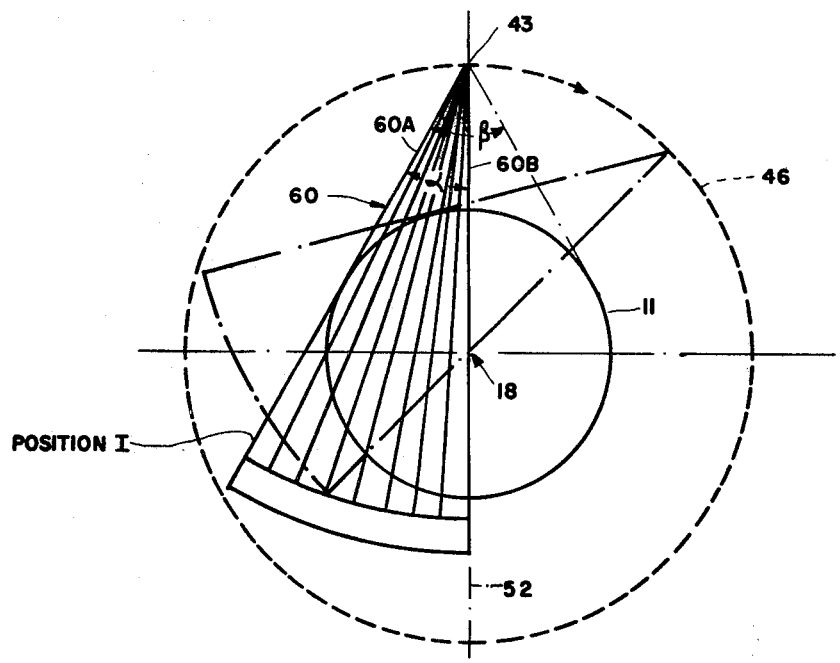
FIG. 3A is a schematic drawing showing what is termed a half-fan beam and the manner in which it completely sweeps out the overall circle of reconstruction during one revolution of the fan beam.
Figure 3B:
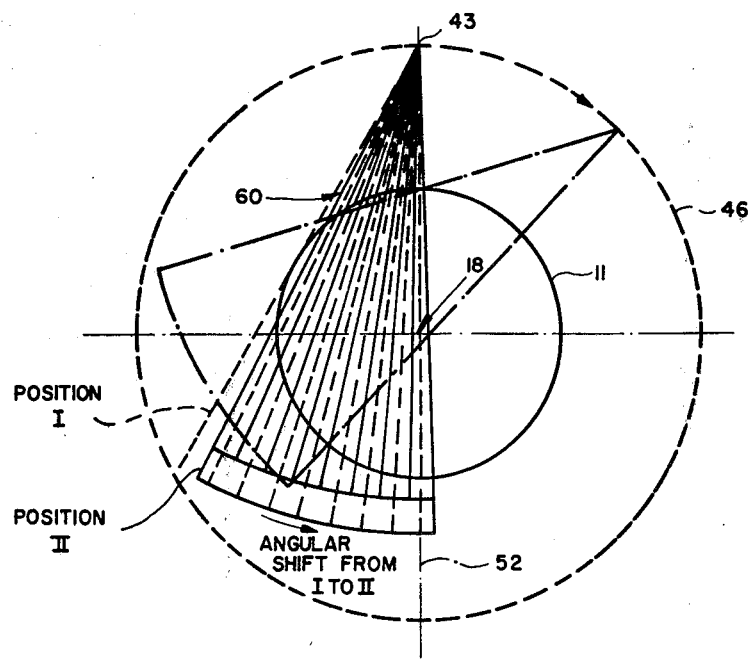
FIG. 3B is similar to FIG. 3A except that the half-fan beam has been rotated through an angle one-half of the angular displacement of the detectors for the purpose of increasing the density of the data points in the circle of reconstruction.

To increase the density of the data and thus provide a more accurate reconstruction, the techniques shown in FIGS. 3B-C can be utilized. In FIG. 3B, position I of fan beam 60 (i.e., the position it occupies in FIG. 3A) is shown in broken lines. By rotating the fan beam about the point 43 through an angle equal to one-half of the angular displacement between the individual beams of the fan beam, the fan beam will occupy position II shown in full lines in FIG. 3B wherein the individual beams of the fan beam will interleave with the chords of the circle of reconstruction 11 through which the beams pass when the fan beam is in position I.

In use, source 43 is rotated on path 46 about the center 18 when the fan beam is in position I (FIG. 3A) to obtain a representation of the absorption distribution associated with a first set of points over the area of circle 11. After the data from this scan are obtained, source 43 is shifted relative to center 18 to position II (FIG. 3B). Thereafter, the source is rotated on path 46 about center 18 to obtain a representation of the absorption distribution associated with a second set of points over the area of circle 11. Thus, a doubling of the density of data points is achieved. In FIG. 3B, the phantom lines show the orientation of the fan beam after a 45° rotation of source 43 about center 18.

Instead of rotating the fan beam about point 43 from position I to position II, the fan beam can be shifted relative to center 18 by linearly displacing the fan beam as shown in FIG. 3C to position III. The shift shown is in a direction perpendicular to line 52 connecting source 43 to center 18 when fan beam 60 is in position I. The shift is only enough for the beams of the fan beam to interleave with the chords of the circle 11 through which the beams passed when the fan beam was in position I. A rotation of source 43 about center 18 when the beam is in position III (FIG. 3C) will also double the density of data points. In FIG. 3C, the phantom lines show the orientation of the fan beam after a 45° rotation of source 43 about new center 18A.

In general, the shifting of the fan beam relative to the center after a rotation is complete (whether a half-fan-beam like that designated 60 is used, or a fractional fan-beam like that designated as 40 is used), can take place in any desired manner. For example, rotation of the fan-beam relative to the source is one approach, as suggested in FIGS. 2B and 3B. Another approach is a linear displacement in a direction perpendicular to a reference axis as suggested in FIGS. 2C and 3C. However, the flexibility of mounting means 13 (FIG. 1) is such that source 43 can be moved in any direction in the plane of cross-section 14.

It should also be realized that the angles $\alpha$ and $\beta$ shown in the drawings are merely illustrative of the angles that can be utilized. In addition, the number of beams shown in the various fan beams of the drawings are only indicative of the fan beams, it being understood that the actual number of beams is dependent on factors outside the scope of the present invention.

Turning now to FIG. 4, a technique for maintaining scanner apparatus 10 in calibration is illustrated. Where the gain of detectors of detector head 26 tends to drift during the time required for source 43 to complete a scan (i.e., one revolution), stabilization can be achieved during the scan by utilizing calibration apparatus 70 with an X-ray tube that remains on throughout the scan. Such apparatus includes chopper 71 for periodically interrupting the individual beams of the fan-beam, and circuitry 72 associated with each detector of detector head 26. Chopper 71 is driven by motor 73 and includes a plurality of spaced vanes 74 impervious to the radiant output of tube 40 and rotatable by the motor about an axis parallel to the medial line of the fan beam. The axis of the chopper is positioned such that the vanes periodically block the radiant output of the tube. The plane of the chopper vanes is between the source 43 of the tube and the circle of reconstruction 11. Preferably, the plane is located between source 43 and pre-collimator 41.

A beam 75, passing through a hole in pre-collimator 41 and emerging from the circle 11, passes through an aligned hole in postcollimator 42, and is incident on a detector 26B of head 26 associated with beam 75. Also incident on detector 26B is the output of a radioactive source 76 mounted within collimator 42 and shielded from the other detectors of head 26. Source 76 has a relatively long half-life so that its radiant output is substantially time-invariant providing a predetermined input to detector 26B at all times.

When a vane 74 blocks beam 75, the output of detector 26A will be due to source 76 alone. During the time beam 75 passes through the circle 11, the output of this detector will be related to the absorption caused by the contents of the circle and the source 76. The output of detector 26B is supplied to synchronizing switch 77 driven by encoder 78 on the shaft of motor 73 such that the output 79 of the switch provides a representation of the data-plus-standard information, and output 80 provides a representation of the standard alone. Output 80 is applied to comparator 81 which generates an error signal when the gain of detector 26B changes from a reference level. The error signal is applied to gain control device 82 which modifies the gain of the detector such that changes are reduced to zero. Finally, the standard intensity is subtracted from the signal in line 79 to provide data that is representative of the absorption of the beam by the contents of the circle of reconstruction.

In order to normalize the data obtained from detector head 26, it is essential to know the intensity of the beams before they enter the circle of reconstruction. Such intensity is obtained by sampling the radiant output of the tube 40 with a detector. The stability of this detector must therefore be maintained if accurate results are to be obtained in computing the reconstruction of the scanned cross-section. To this end, circuitry 83 associated with detector 84 is utilized. Detector 84 receives a portion of the output of tube 40 through a fixed attenuator 85, such portion being periodically interrupted by the rotating vanes 74 of chopper 71.

Also incident on detector 84 is radiation from a standard source 86 which is similar to source 76. The operation of circuitry 83 is similar to the operation of circuitry 72 with the result that the gain of detector 84 is stabilized in the same way as the gain of detector 26B is stabilized.

When a pulsed X-ray tube is used as a source in the scanner head assembly, mechanical chopper 71 is not needed. The chopping of the beams necessary to the calibration process is achieved by the pulsed operation of the tube. Thus, the term "beam chopper" is used to denote mechanical chopper 71 in the environment shown in FIG. 4 where the X-ray tube remains on during the scanning regimen, or a pulsed X-ray tube when the latter is used.

As a further optional feature, reconstruction of a periodically moving object can be achieved by collecting data only during the same phase of movement. If the object is living, a physiological parameter of the object, such as heart beat, can be monitored by a transducer as indicated by reference numeral 7 in FIG. 1. Monitor 6 responds to the transducer output by enabling gates 5 only during the same phase of the parameter.

With regard to the algorithm by which data obtained during a scan can be reduced to provide the reconstructed cross-section, one such algorithm is the circular harmonic transform (CHT) of reference [1] because this algorithm is well adapted to a pure rotational scan. It is based on finite sampling along arcs in shadow space which correspond to integrating a rotating beam. The CHT algorithm for reconstructing a cross-section is based on assuming that its shadow can be expressed as a linear combination of the circular harmonics of the shadow. The cross-section is reconstructed by applying the inverse of the shadow operator based on this assumption.

Other algorithms can also be used with the scanning technique disclosed herein. For example, reconstruction via successive approximation as disclosed in U.S. Pat. No. 3,934,142 could be used. Alternatively, reconstruction can be by way of direct fan convolution, plane-waves or the Radon inversion formula. In addition, re-sorting of shuffling of the data obtained during the pure rotational scan can be carried out to permit the conventional parallel-beam algorithm to be employed for processing the data and obtaining the desired reconstruction. Other techniques are shown in reference [2].

It is believed that the advantages and improved results furnished by the method and apparatus of the present invention are apparent from the foregoing description of the several embodiments of the invention. Various changes and modifications may be made without departing from the spirit and scope of the invention as sought to be defined in the claims that follow.

What is claimed is:

1. In apparatus for calibrating a scanner of the type having a source for producing at least one pencil beam of penetrating radiation originating at essentially a point and passing through a cross-section to be reconstructed, a detector mounted in predetermined relationship to the source for measuring the intensity of the beam emerging from the cross-section, and means for rotating the source in a circular path coplanar with the cross-section, the improvement comprising means for periodically interrupting the beam during rotation of the source through a portion of the revolution, and means responsive to radiation from a reference source incident on the detector for calibrating the detector during the interval that the beam is interrupted.

2. The improvement of claim 1 wherein the source is a pulsable X-ray tube and the pulser for pulsing the tube constitutes the means for interrupting the beam.

3. The improvement defined in claim 1 further comprising:
   (a) a first reference source for providing a predetermined amount of radiation to the detector;
   (b) a beam chopper for periodically interrupting the beam;
   (c) a gain controller responsive to an error signal for controlling the gain of the detector; and
   (d) means responsive to the beam chopper for supplying an error signal to the gain controller while the beam is interrupted and the detector receives radiation from only the first reference source.

4. The improvement defined in claim 3 wherein the source producing the beam is an X-ray tube, and the improvement comprising detector means for receiving a portion of the radiant output of the tube; a second standard reference source for providing a predetermined amount of radiation to the detector means; an output chopper for periodically interrupting radiation reaching the detector means from the tube; and intensity control circuit responsive to an error signal for controlling the radiant output of the tube; and means responsive to the output chopper for supplying an error signal to the intensity control circuit when radiation from the tube is prevented from reaching the detector means and the latter receives radiation from only the second reference source.

5. Apparatus according to claim 4 wherein the beam chopper and the output chopper are the same.

6. A method for scanning a body as part of a process for reconstructing a cross-section thereof using a source of penetrating radiation that produces a plurality of coplanar beams defining a fan beam passing through the body coplanar with the cross-section, the method comprising:
   (a) positioning the fan beam relative to a spatially fixed center at a first position;
   (b) rotating the fan beam about the fixed center and measuring the intensity of each beam after it passes through the cross-section;
   (c) repositioning the fan beam relative to the fixed center to a second position; and
   (d) repeating step (b).

7. The method of claim 6 wherein the rotations are through substantially 360° and each rotation causes the fan beam to sweep out an area of the cross section defined by reference circles concentric with the fixed center and tangent to the extremities of the fan beam.

8. The method of claim 7 wherein the positions of the fan beam are selected such that the swept out areas overlap.

9. The method of claim 7 wherein the positions of the fan beam are selected such that the swept out areas are contiguous.

10. The method of claim 7 wherein the two positions of the fan beam are related by rotation of the fan beam about its apex.

11. The method of claim 7 wherein the two positions of the fan beam are related by translation of the fan beam.

12. In apparatus for calibrating a scanner of the type having a source for producing a fan beam of penetrating radiation co-planar with a cross section to be reconstructed, a plurality of detectors mounted in predetermined relationship to the source for measuring the x-ray transmissivity of the cross-section, and means for rotating the fan beam about a center perpendicular to the cross-section the improvement comprising alternately applying to the detectors during rotation of the fan beam through one revolution, reference radiation that is independent of the angular position of the fan beam and dependent on the angular position of the fan beam.

13. The improvement of claim 12, wherein calibration is achieved by adjusting the gain of the detectors.

14. In a method for scanning a body to enable a cross-section thereof to be reconstructed by: (a) producing from a point source of penetrating radiation, a fan beam of the type described having an apical angle $\alpha$ and being coplanar with and passing through the cross-section; (b) rotating the fan beam through one revolution about a spatially fixed center for causing the fan beam to sweep out an area in the plane of the cross-section, the area being contained within a reference circle tangent to the extremities of the fam beam most remote from the fixed center, and the tangents to the reference circle passing through the source intersecting at an apical angle $\beta$; and (c) computing the absorption coefficients over such area from measurements of the intensities of the beams of the fan beam;

the improvement comprising the steps of selecting the apical angle $\alpha$ such that it is less than the apical angle $\beta$, and shifting the fan beam, upon completion of one revolution, relative to the fixed center, and again carrying out steps (b) and (c).

15. The improvement defined in claim 14 wherein the fan beam is shifted by rotating about an axis perpendicular to the fan beam and passing through the source.

16. The improvement defined in claim 15 wherein the rotation of the fan beam is through an angle about half the angle between the individual beams of the fan beam.

17. The improvement defined in claim 15 wherein the fan beam is rotated through an angle $\alpha$ upon completion of one revolution.

18. The improvement defined in claim 17 including the step of relating the intensity of radiation entering the area swept out by the fan beam during a revolution thereof to the path length of the fan beam through such area.

19. The improvement defined in claim 15 including the step of monitoring the intensity of the extremity of the fan beam most remote from the fixed center during each revolution of the fan beam, and rotating the fan beam through an angle $\alpha$ upon completion of one revolution only if the monitored intensity exceeds a threshold over a predetermined portion of the revolution.

20. The improvement defined in claim 14 wherein the fan beam is shifted by linearly displacing it relative to the fixed center.

21. The improvement defined in claim 14 wherein the apical angle $\alpha$ is selected such that is is approximately half the apical angle $\beta$.

22. The improvement defined in claim 21 further comprising shifting the fan beam relative to the fixed center, and again carrying out steps (b) and (c).

23. The improvement defined in claim 22 wherein the source is shifted by linearly displacing it relative to the fixed center.

24. The improvement defined in claim 22 wherein the fan beam is shifted by rotating it about an axis perpendicular to the fan beam and passing through the source.

25. The improvement defined in claim 24 wherein the rotation of the fan beam is through an angle about half the angle between the individual beams of the fan beam.

26. The improvement defined in claim 24 wherein the rotation of the fan beam is through an angle about equal to $\alpha$.

27. The improvement defined in claim 14 wherein the apical angle $\alpha$ is selected such that $\alpha=\beta/2n$ where $n=1, 2, 3, \ldots$, and further comprises carrying out steps (b) and (c) n times, and rotating the fan beam, after completion of the steps, $n-1$ times in the plane thereof about the source and through an angle $\alpha$.

28. The improvement defined in claim 14 wherein the absorption coefficients are computed using the circular-harmonic-transform.

29. Apparatus for scanning a body to enable a cross-section thereof to be reconstructed comprising:
(a) a movable head assembly having a point source of penetrating radiation for producing a fan beam of the type described having an apical angle $\alpha$, and which is coplanar with, and passes through, the cross-section;
(b) driver means for rotating the head assembly about a spatially fixed center for causing the fan beam to sweep out of area in the plane of the cross-section, the area being contained within a reference circle tangent to the extremities of the fan beam most remote from the fixed center, the tangents to the reference circle passing through the source intersecting at an apical angle $\beta$;
(c) the apical angle $\alpha$ being less than the apical angle $\beta$; and
(d) means for shifting the head assembly relative to the fixed center and in the plane of the fan beam.

30. Apparatus according to claim 29 wherein the movable head assembly also includes a planar array of detectors spatially fixed relative to the source and located at discrete angular positions with respect to the source.

31. Apparatus according to claim 30 wherein the movable head assembly also includes a pre-collimator interposed between the source and the swept-out area.

32. Apparatus according to claim 29 wherein the intensity of radiation entering the area swept out by the fan beam is adjustable, and including means for rotating the head assembly through an angle $\alpha$ about an axis perpendicular to the fan beam and passing through the source upon completion of one revolution of the head assembly, and means for relating the intensity of radiation entering the area swept out by the fan beam to the path length of the fan beam through such area.

33. Apparatus according to claim 29 wherein the apical angle $\alpha$ is approximately half the apical angle $\beta$.

34. Apparatus according to claim 33 including means responsive to the output of the detector associated with the extremity of the fan beam most remote from the fixed center for halting rotation of the head assembly upon completion of one revolution if the output exceeds a threshold over a predetermined portion of the revolution, and for rotating the head assembly through an angle $\alpha$ abut an axis perpendicular to the fan beam and passing through the source upon completion of one revolution if the output is below a predetermined threshold over a predetermined portion of the revolution.

* * * * *

Notice of Adverse Decision in Interference

In Interference No. 100,881, involving Patent No. 4,149,079, D. Ben-Zeev and D. Inbar, METHOD OF AND MEANS FOR SCANNING A BODY TO ENABLE A CROSS-SECTION THEREOF TO BE RECONSTRUCTED, final judgment adverse to the patentees was rendered Aug. 28, 1984, as to claims 6, 7, 9, 14 and 21.

[*Official Gazette November 19, 1985.*]